United States Patent
Fourtillan et al.

(10) Patent No.: US 10,744,122 B2
(45) Date of Patent: Aug. 18, 2020

(54) TRANSDERMAL THERAPEUTIC SYSTEM CONTAINING VALENTONIN AND USE THEREOF AS A MEDICAMENT

(71) Applicant: Soeur Josefa Menendez, Poitiers (FR)

(72) Inventors: Jean-Bernard Fourtillan, Poitiers (FR); Marianne Fourtillan, Poitiers (FR)

(73) Assignee: Soeur Josefa Menendez (FR)

( * ) Notice: Subject to any disclaimer, the term of this patent is extended or adjusted under 35 U.S.C. 154(b) by 0 days.

(21) Appl. No.: 15/548,502

(22) PCT Filed: Feb. 4, 2016

(86) PCT No.: PCT/EP2016/052376
§ 371 (c)(1),
(2) Date: Aug. 3, 2017

(87) PCT Pub. No.: WO2016/124688
PCT Pub. Date: Aug. 11, 2016

(65) Prior Publication Data
US 2018/0000796 A1    Jan. 4, 2018

(30) Foreign Application Priority Data
Feb. 4, 2015 (EP) .................................... 15305161

(51) Int. Cl.
*A61K 9/70* (2006.01)
*A61K 31/44* (2006.01)
*A61K 31/437* (2006.01)
*A61K 31/4045* (2006.01)

(52) U.S. Cl.
CPC .......... *A61K 31/437* (2013.01); *A61K 9/7092* (2013.01); *A61K 31/4045* (2013.01)

(58) Field of Classification Search
CPC ............................ A61K 31/437; A61K 9/7084
USPC ........................................ 514/292; 424/449
See application file for complete search history.

(56) References Cited

U.S. PATENT DOCUMENTS 6,048,868 A    4/2000    Fourtillan et al.

FOREIGN PATENT DOCUMENTS

| FR | 2898358 A1 | 9/2007 |
|----|------------|--------|
| WO | 2007101863 A1 | 9/2007 |

OTHER PUBLICATIONS

Kanikkannan et al. "Formulation and In vitro Evaluation of transdermal patch of Melatonin," Drug Development and Industrial Pharmacy, 2004, vol. 30, No. 2, pp. 205-212 (Year: 2004).*
Cilurzo et al. "Adhesive properties: a critical issue in transdermal patch development," Expert Opinion on Drug Delivery, 2012, vol. 9, No. 1, pp. 35-45 (Year: 2012).*
Mangialasche et al. "Alzheimer's disease: Clinical trials and drug development," Lancet Neurology, 2010, vol. 9, pp. 702-716 (Year: 2010).*
WO 2007/101863 A1 English (Machine) Translation, 2007 (Year: 2007).*
International Search Report from Application No. PCT/EP2016/052376, dated Mar. 30, 2016.
Fourtillan, J.B., et al., Melatonin secretion occurs at a constant rate in both young and older men and women., Am. J. Physiol. Endocrinol. Metab., Jan. 2001, pp. E11-E22, vol. 280, No. 1.

* cited by examiner

*Primary Examiner* — Shengjun Wang
(74) *Attorney, Agent, or Firm* — Lerner, David, Littenberg, Krumholz & Mentlik, LLP

(57) ABSTRACT

The invention relates to an adhesive transdermal therapeutic system containing, as an active principle, an association of valentonin (VLT) and 6-methoxyharmalan (6-MH).

11 Claims, No Drawings

TRANSDERMAL THERAPEUTIC SYSTEM CONTAINING VALENTONIN AND USE THEREOF AS A MEDICAMENT

CROSS REFERENCE TO RELATED APPLICATIONS

The present application is a national phase entry under 35 U.S.C. § 371 of International Application No. PCT/EP2016/052376, filed Feb. 4, 2016, published in French, which claims priority from European Patent Application No. 15305161.0 filed Feb. 4, 2015, the disclosures of which are incorporated herein by reference.

The present invention relates to an adhesive transdermal therapeutic system containing as active ingredient a combination of valentonine (VLT) and 6-methoxyharmalan (6-MH).

The present invention relates more particularly to the treatment of sleep disorders and primary insomnia, depression, psychosis, as well as Parkinson's disease and Alzheimer's disease.

It should be recalled that there are two types of sleep: physiological sleep and anesthetic sleep. Only physiological sleep, recognizable by its EEG trace, is restorative to the body.

Physiological sleep is recognizable by characteristic EEG traces. It comprises deep slow-wave sleep, which is restorative, and paradoxical sleep (also called rapid-eye-movement or REM sleep), which appears important for memory.

Physiological sleep occurs when the level of alertness falls below a certain threshold, with loss of consciousness. For humans and other diurnal animals, under normal conditions (in the absence of depression, for example), during the nychthemeron, this phenomenon occurs when concentrations of valentonine (VLT), the hormone of the sleep state (also referred to herein as the sleep hormone), are higher than those of 6-methoxyharmalan (6-MH), the hormone of the waking state (also referred to herein as the waking hormone). This prevalence of VLT over 6-MH exists during the phase of night-time darkness (in France generally between 10 p.m. and 6 a.m.) regardless of the season (Fourtillan J B, Brisson A. M., Gobin P., Fourtillan M., Ingrand I., Decourt J. Ph. and Girault J., Melatonin secretion occurs at a constant rate in both young and older men and women. Am. J. Physiol. Endocrinol. Metab., 280, E11-E22 (2001)). During this rest period, this prevalence of VLT, relative to 6-MH, results from the pharmacokinetic properties of these two hormones. In dogs, it was possible to determine the pharmacokinetic parameters of VLT and 6-MH.

The mean values (±standard deviations) of the main parameters characteristic of the distribution and elimination kinetics of the two hormones are shown below:

Valentonin:
$T_{1/2}z$=0.70 (±0.17) h
MRT=0.49 (±0.16) h
$V_d$ss=40 (±21) liters
CL=79.0 (±19.9) liters/hour.

6-Methoxyharmalan:
$T_{1/2}z$=2.27 (±0.91) h
MRT=1.31 (±0.45) h
$V_d$ss=120 (±51) liters
CL=89.19 (±22.9) liters/hour.

It is highly likely that the pharmacokinetic parameter values of both the elimination kinetics ($T_{1/2}z$ and CL) of VLT and 6-MH and their distribution kinetics (MRT and $V_d$ss) are identical in humans and all other diurnal animals, such as dogs.

During the period when VLT is prevalent over 6-MH, sleep results from allosteric activation of $5\text{-HT}_{2c}$ serotonin receptors by VLT. Furthermore, during nocturnal sleep, VLT activates, by allosteric modulation, the $\alpha_2$-adrenergic receptors of the central nervous system, which lowers blood pressure and heart rate during the rest period, as well as the $D_1$ and/or $D_2$ dopamine receptors, with muscle relaxation. Other selective allosteric activations are likely to take place during the night.

At the end of the period of secretion, around 6 a.m., 6-methoxyharmalan concentrations quickly become higher than those of valentonin, notably because 6-MH elimination is much slower ($T_{1/2}z$=2.27 h) than that of VLT ($T_{1/2}z$=0.70 h). The prevalence of 6-MH over VLT results in the blocking of $5\text{-HT}_{2c}$ serotonin receptors, between 6 a.m. and 10 p.m., awakening occurring when alertness exceeds a certain threshold specific to each individual. Selective blocking of $5\text{-HT}_{2c}$ serotonin receptors, $\alpha_2$-adrenergic receptors and $D_1$ and/or $D_2$ dopamine receptors thus makes it possible to increase the level of alertness, and therefore to ensure awakening, to increase blood pressure and heart rate, and to increase muscle tonus.

Artificial or anesthetic sleep is completely different from natural or physiological sleep. Its EEG trace comprises mainly light fast-wave sleep, which is not restorative to the body, with little deep sleep. A collapse of the proportions of paradoxical sleep, in correlation with the side effects of anterograde amnesia, is observed in patients.

Artificial or anesthetic sleep is, for example, induced by benzodiazepines (diazepam, etc.) and related drugs (zolpidem, zopiclone). All these compounds have the following pharmacological properties in common:

they are activators by allosteric modulation of $GABA_A$ergic receptors, whose activation produces neuroinhibitory effects. The result is a lowering of alertness as if under anesthesia, and at the same time, they are serotonin antagonists of $5\text{-HT}_{2c}$ serotonin receptors. They block these receptors, like 6-methoxyharmalan, the waking hormone, and LSD. The reason for this action is simple: they have in their chemical structures the pharmacophore features of 6-MH.

Consequently, unfortunately, these compounds have two contradictory pharmacological actions:

by their $GABA_A$ergic stimulation, they produce poor sleep, i.e., little deep sleep and a collapse of paradoxical sleep; and, by blocking $5\text{-HT}_{2c}$ serotonin receptors, they antagonize physiological sleep, by acting as the waking hormone, 6-MH. Therefore, they have depressogenic and anxiogenic effects and, in this way, they antagonize the anxiolytic effects of their $GABA_A$ergic actions and the effects of antidepressants.

It was previously discovered (FR 2 898 358) that during the nocturnal sleep period (between 10 p.m., when secretion begins, and 6 a.m., when secretion ends), and regardless of the season, melatonin produced by the pineal gland, following a first acetylation of serotonin, facilitated by N-acetyltransferases, undergoes, at the moment it is produced, a second step of enzymatic acetylation by N-acetyltransferases, giving successively two β-carboline derivatives, namely 6-methoxy-1-methyl-3,4-dihydro-β-carboline, called 6-methoxyharmalan (6-MH), and 2-acetyl-6-methoxy-1-methylene-3,4-dihydro-β-carboline, called valentonin (VLT).

Thus, the sleep-wake system functions with these three hormones: melatonin (MLT), valentonin (VLT) and 6-methoxyharmalan (6-MH). Melatonin being the precursor of VLT and 6-MH, it is also the marker. Therefore, the state of the sleep-wake system can be known by measuring plasma MLT concentrations in patients. Pharmacokinetic studies of pineal secretion (Am. J. Physiol. Endocrinol. Metab., 280, E11-E22 (2001)) in 12 young volunteer subjects and 12 older volunteer subjects, showed high variability in the secretion rates, and therefore in the amounts secreted, of MLT in proportions of 1 to 10, depending on the subjects. This high variability is undoubtedly the cause of many of the neurological disorders observed in humans, such as primary insomnia, sleep disorders, reactive and endogenous depression, neurodegenerative diseases (Parkinson's, Alzheimer's), and psychosis.

The treatment of depression, psychotic states, Parkinson's disease and Alzheimer's disease must include an understanding of this same sleep-wake system. Explanations of the mechanisms of these disorders, and of the modes of action of their new treatments, have not been based on knowledge of the mechanism of physiological sleep. Indeed, it was thought that excess dopamine was the cause of psychosis, whereas it has just been discovered that it is excess 6-methoxyharmalan, the waking hormone, that is the cause of psychotic states. Depression, at least reactive depression, is not an incurable condition, because it is always alleviated by strengthening the sleep-wake system. Neurodegenerative diseases, such as Parkinson's disease and Alzheimer's disease, are in reality caused by a quantitative deficit of the sleep-wake system.

Thus, these conditions could undoubtedly be prevented and stopped in their progression. In Alzheimer's disease, sleep and cognition could be restored by administering a valentonergic and 6-methoxyharmalan.

The [(VLT)-(6-MH)] system thus plays an essential part by regulating the body's mental and vegetative states during the 24 hours of the nychthemeron.

The harmonious functioning of this system is directly related to:
- the chemical structures of the sleep hormone (VLT) and the waking hormone (6-MH), which enable them to stimulate (VLT), during the nocturnal rest period, or to selectively block (6-MH), the receptors involved in regulation of the organs and physiological processes that function differently during the rest and activity periods;
- the pharmacokinetic properties of valentonin and 6-methoxyharmalan, which make it possible to ensure the prevalence of VLT, during the 8 hours of the sleep period, between 10 p.m. and 6 a.m., and the prevalence of 6-MH, during the waking or activity period, between 6 a.m. and 10 p.m.;
- the change in the concentrations of VLT and 6-MH, corresponding to constant-rate infusion into the bloodstream, during the 8 hours of secretion of the two hormones by the pineal gland.

The Applicant thus sought to implement a hormone replacement therapy based on VLT, in combination with 6-MH, with the aim of regulating the functioning of the body according to each patient's profile, which can be established by a method for assaying plasma melatonin concentrations in a blood sample taken between 10 p.m. and 6 a.m., preferably from 1 a.m. onwards.

Since valentonin, like most endogenous compounds, cannot be administered orally, the present invention relates to a transdermal therapeutic system of one or both of the above-mentioned hormones, advantageously in the form of single- or dual-compartment patches, for the treatment of neurological disorders resulting from a quantitative deficit or excess of the [(VLT)-(6-MH)] system.

Thus, the invention relates to a transdermal therapeutic system containing as active ingredient a combination of valentonin (VLT) and 6-methoxyharmalan (6-MH), which may be, in a manner known per se, in the form of a single- or dual-compartment patch or a matrix patch.

Preferably, the invention relates to an adhesive transdermal therapeutic system containing a combination of a load of valentonin (VLT) and of 6-methoxyharmalan (6-MH) capable of delivering into the bloodstream valentonin and 6-methoxyharmalan in a [VLT]/[6-MH] mass proportion equal to 4 during the application period of the patch, preferably for about 8 to 10 hours.

The practical embodiment of the patches will be determined by a person skilled in the art, based on his general knowledge of the subject, so as to obtain a controlled and extended systemic administration of valentonin and 6-methoxyharmalan, throughout the application period of the patch, i.e., for a period of about 8 to 10 hours.

Generally, by making use of his general knowledge of the subject, a person skilled in the art will be able to integrate the two active ingredients into two independent patches and mix the two ingredients either in the same matrix or in superimposed matrices, or in matrices assembled adjacently on the same protective film. Of course, valentonin and 6-methoxyharmalan may also be present in another type of two-independent-reservoir patch.

It may be recalled generally that there are two main classes of transdermal therapeutic systems or patches, both of which consist of:
- an impermeable outer layer,
- a compartment containing the active ingredient,
- a means for controlling the release of the active ingredient (s),
- an adhesive component for maintaining the patch on the application area of the skin, and
- a protective support designed to be removed just before applying the patch.

The patch according to the present invention may thus be designed with either a reservoir-type or a matrix-type conformation.

The reservoir-type patch will comprise one or two separate reservoir(s) containing the active ingredient(s) in solution or in suspension in the polymer matrix coming into contact with the skin by means of a semipermeable polymeric membrane used to adjust the release rate of the active ingredient(s).

The matrix-type patch will comprise a polymeric mass inside of which the active ingredient(s) will be dissolved or dispersed in suitable proportions. These active ingredients are released via diffusion through the polymer chains of said matrix.

According to a particular embodiment of this type of patch, the adhesive covers the totality of the release surface of the matrix and forms an integral part thereof. This is an active-adhesive-type patch, well-known to a person skilled in the art, arising from a simplified manufacturing process that makes it possible to produce thin and suitably flexible patches for comfortable application to the patient's skin.

In an advantageous embodiment of the present invention, valentonin and 6-methoxyharmalan are disposed in separate reservoirs, brushing aside any problem of stability or any other risk of interactions capable of altering the relative diffusion fluxes of the active ingredients when they are packaged mixed together in the same matrix.

In a particular embodiment of the invention of a dual-compartment patch, each compartment of the patch may contain a polymer matrix containing each of the two active ingredients in isolation. To ensure satisfactory infusion of these active ingredients into the bloodstream at the appropriate dose, a person skilled in the art will easily be able to set the following parameters:

the area and volume ratios of each compartment of the patch;
possible addition of a hydrophilic additive;
possible addition of an absorption promoter; and,
more generally, any type of additives well-known to a person skilled in the art for controlling the fluxes of valentonin and 6-methoxyharmalan.

In a manner known per se, such a patch comprises a peelable protective film designed to preserve the adhesive face to be applied to the skin from the time the patch is manufactured to the end of its shelf life. In a manner known per se, a person skilled in the art will have for example recourse to polyester films, one face of which may be treated with anti-adhesive silicones.

The adhesive polymer matrix containing valentonin and 6-methoxyharmalan may be of the polymer or copolymer type, for example the polyisobutylene or polyacrylic type, the ethylene-vinyl acetate copolymer type, or the silicone polymer type.

Self-curing acrylic resins, for example of the Duro-Tak® type (marketed by Henkel), will be used in a conventional manner.

As indicated above, absorption promoters may be used in a manner known per se. Examples of such additives include monoalkyl ethers of diethylene glycol, saturated polyglycolized glycerides, 1,2-propanediol and ethanol.

Since valentonin and 6-methoxyharmalan are lipophilic, it may also prove necessary to introduce into the polymer matrix hydrophilic additives such as natural or synthetic polymers, such as guar gum, xanthan gum or polyvinylpyrrolidone.

According to a particular embodiment of the present invention, the adhesive layer containing the active ingredients, the subject-matter of the present invention, contains one or more alkyl(meth)acrylate-based copolymers, in particular ethyl methacrylate, n-octyl methacrylate and dodecyl methacrylate. Other monomers may be added to this alkyl (meth)acrylate copolymer, in particular the monomers acrylonitrile, vinyl acetate, vinyl propionate or 1-vinyl-2-pyrrolidone.

To ensure the stability of the active ingredients within the matrices of the patch and in particular to avoid any risk of degradation by oxidation during storage, small proportions of an antioxidant agent such as α-tocopherol and ascorbyl palmitate will advantageously also be added.

In the context of the present invention, the Applicant was able to determine that the main indications for administration of valentonin alone or in combination with 6-MH can be classified into two main categories:

A) Conditions resulting from a quantitative deficit of the [(VLT)-(6-MH)] system:
primary insomnia;
sleep disorders;
endogenous and reactive depression; and,
neurodegenerative diseases (Parkinson's, Alzheimer's, etc.).

It is clear that conditions due to a deficit of the [(VLT)-(6-MH)] system can be treated with a combination of valentonin, bioavailable for the chosen route of administration, and 6-methoxyharmalan.

The pharmacokinetic properties of valentonin and 6-MH, and in particular their bioavailabilities for the chosen route of administration, must make it possible, given that it is a matter of a hormone replacement therapy comprising two hormones, to reproduce as closely as possible the curves of the change in plasma concentrations of the two hormones of the [(VLT)-(6-MH)] system, for 24 hours.

For a hormone replacement therapy consisting of two hormones (VLT and 6-MH), one of which, valentonin, is unstable since it is completely hydrolyzed in acidic gastric medium, the route of administration selected in the context of the present invention is the transdermal route, for the following reasons:

1) Just like the intravenous route (much too restrictive, because reproducing the physiological curves of the change in plasma levels of the two hormones would require intravenous perfusion of the two-hormone mixture during the 8 hours of nocturnal rest, between 10 p.m. and 6 a.m.), the transdermal route makes it possible to administer the two natural hormones (valentonin and 6-methoxyharmalan) simultaneously in the form of a single transdermal patch. For the treatment of conditions resulting from a quantitative deficit of the [(VLT)-(6-MH)] system, it may thus be envisaged to apply a patch during the 8 hours of the period of pineal secretion of the two hormones, between 10 p.m. and 6 a.m., in suitable proportions.

2) Furthermore, the use of patches having two separate reservoirs (one reservoir for each hormone) should make it possible to control the releases of the two hormones separately, without them interfering with each other in terms of their bioavailabilities and the lability of the combination of the two products brought into contact.

In the case of application to primary insomnia and similar conditions, one observes an insufficient secretion of valentonin (VLT) and, in parallel, of 6-methoxyharmalan (6-MH), resulting from a too-low pineal secretion of melatonin. In such a case, an assay of melatonin, as a marker of the two hormones of the [(VLT)-(6-MH)] system in the plasma, during the night, will make it possible to determine the deficit quantitatively and consequently to adapt the dosages of valentonin and 6-MH in the combination.

For the other indications, such as sleep disorders, depression, neurodegenerative diseases (Parkinson's, Alzheimer's), it also appears necessary to administer combinations of valentonin and 6-methoxyharmalan. These pathologies correspond to a quantitative deficit of the VLT/6-MH system. The magnitude of this deficit varies with the condition. It can be evaluated by assaying melatonin at the steady-state before 6 a.m., as a marker of the [(VLT)-(6-MH)] system.

It should be recalled that under physiological conditions, the two hormones of the [(VLT)-(6-MH)] system and melatonin are delivered by the pineal gland into the bloodstream for 8 hours, between 10 p.m. and 6 a.m., as a constant-rate intravenous perfusion, i.e., having zero-order kinetics. The change in the concentrations of the two hormones in the blood plasma depends on their pharmacokinetic properties, and in particular their elimination kinetics, characterized by their terminal half-life ($T_{1/2}z$). Thus, for each hormone (VLT and 6-MH) secreted by the pineal gland in a variable manner for each subject, the change in plasma concentrations depends on:

the secretion rate, which reflects, for each subject, and from a quantitative point of view, the level of said subject's [(VLT)-(6-MH)] system. This datum is specific to each subject. The value of this individual datum varies with the neurological disorder from which each patient suffers; and, the pharmacokinetic characteristics of the two hormones. It is indeed highly likely that the elimination and distribution kinetics are identical in humans and all diurnal animals, such as dogs, in which valentonin and 6-methoxyharmalan have half-lives ($T_{1/2}z$) equal to 0.70 h and 2.27 h, respectively, and volumes of distribution equal to 5 liters/kg and 15 liters/kg, respectively.

It can thus be anticipated, for the treatment of conditions resulting from a deficit of the [(VLT)-(6-MH)] system, to have different dosages of valentonin and 6-methoxyharmalan in the two reservoirs of the patches, according to the type of condition and the melatonin levels observed in the patients.

B) The invention also extends to the treatment of conditions resulting from a quantitative excess of the [(VLT)-(6-MH)] system, in particular psychotic states.

The treatment of psychosis caused by excess 6-methoxyharmalan between 6 a.m. and 10 p.m., during the day, may be envisaged by displacement of excess 6-MH by valentonin, during this period. This treatment has never been claimed. It is an indication for which valentonin should be administered alone.

According to a first aspect of the invention, the adhesive transdermal therapeutic system contains valentonin (VLT) as active ingredient.

In the context of the present invention, the doses of valentonin (VLT) and 6-methoxyharmalan (6-MH) in the combinations of the two hormones, administered transdermally, were established.

The most common neurological disorders (primary insomnia, sleep disorders, reactive and endogenous depression, and neurodegenerative diseases such as Parkinson's and Alzheimer's) are due to quantitative deficits of the [(VLT)-(6-MH)] system that will need to be restored.

The present invention thus relates to the treatment of conditions due to quantitative deficits of the hormones of the [(VLT)-(6-MH)] system.

To ensure and maintain, harmoniously, and exactly like the physiology, satisfactory regulation of the body's mental and vegetative states during the 24 h of the nychthemeral cycle, it is imperative to administer the combination (VLT+6-MH) in a form capable of reproducing pineal secretion of the two hormones between 10 p.m. (or when the patient goes to bed) and 6 a.m. (or when the patient gets up). This makes it necessary to observe the following requirements:

1. Administration of the physiological hormones, valentonin and 6-methoxyharmalan, and not their synthetic substitutes. Indeed, chemically different, the synthetic substitutes have different pharmacokinetic properties that would make it impossible to alternate the periods of prevalence of each hormone, at the exact moment at the end of the rest periods (6 a.m., or upon rising) and the activity periods (10 p.m., or at bedtime). This requirement necessitates very precise and matching pharmacokinetic profiles for the two natural hormones (VLT and 6-MH). This is all the more so as these concentration prevalences must exist during the two periods, not only in the plasma, but also at the sites of action of the two hormones (5-$HT_{2c}$, $\alpha_2$, $D_1$ and $D_2$ receptors, etc.).

2. The mode of administration must reproduce a constant-rate infusion of the two hormones lasting 8 hours (between 10 p.m., at bedtime, and 6 a.m., upon rising). Since an 8-hour endovenous perfusion is too restrictive, and since VLT is completely degraded in acidic gastric medium, the extravascular route capable of providing such an infusion in the context of the present invention is the transdermal route, in the form of dual-reservoir patches applied for 8 hours starting at bedtime and removed upon rising.

3. The bioavailable doses of VLT and 6-MH that must be released into the body from the patch can be calculated for each condition treated, based on the values of the plasma melatonin levels measured between 1 a.m. and 6 a.m. in the patients to be treated.

During a study of the kinetics of melatonin secretion by the pineal gland carried out in humans, in two groups of 12 healthy volunteer subjects of both sexes, young and older (Fourtillan J B, Brisson A. M., Gobin P., Fourtillan M., Ingrand I., Decourt J. Ph. and Girault J., Melatonin secretion occurs at a constant rate in both young and older men and women. Am. J. Physiol. Endocrinol. Metab., 280, E11-E22 (2001)), it was possible to measure the total amounts of melatonin (MLT) secreted during the night (between 10 p.m. and 6 a.m.). A large interindividual variation (from 1 to 10) in the 24 subjects was observed. This study showed that the total amount of MLT secreted, during the 8 hours of the night, adds up to an average of 28.7 µg (35.7 µg in healthy young adult men weighing an average of 74 kg, or 0.48 µg/kg; and 21.6 µg in healthy young adult women weighing an average of 54 kg, or 0.40 µg/kg) for an average weight equal to 64 kg, or a total secretion of MLT equal to 0.44 µg/kg. Furthermore, in these 12 young subjects, the total amounts of MLT secreted during the night vary from 10 to 60 µg, corresponding to maximum plasma concentrations, observed from 1 a.m. onwards, ranging between 19 and 93.7 pg/ml, with a mean value equal to 54.5 pg/ml. In the 12 older subjects, the maximum plasma concentrations observed from 1 a.m. onwards were between 9.6 and 124.7 pg/ml, with a mean value equal to 45.6 pg/ml. On average, the maximum plasma MLT concentrations are lower in older persons, although the maximum limit value (124.7 pg/ml) is observed in an older person.

This study makes it possible to locate the mean total amount of melatonin secreted by the pineal gland during the night (mean duration equal to 8 h, regardless of the season) at about 30 µg, or 0.5 µg/kg, in the healthy young adult subjects of both sexes. It should be kept in mind that there is a very large interindividual variability for this biological parameter. Indeed, this secretion varies from 10 to 60 µg in the sample of 12 healthy young adult volunteer subjects (6 men, 6 women) corresponding to maximum plasma concentrations observed from 1 a.m. onwards ranging between 19 and 93.7 pg/ml.

It is not possible to measure nocturnal pineal MLT secretions in patients, but this study, carried out in young and older individuals, shows that in the 24 subjects studied, the maximum plasma melatonin concentrations observed from 1 a.m. onwards vary from 9.6 to 124.7 pg/ml. These levels reflect total pineal MLT secretions.

The important thing to remember about this study is that the total pineal secretion of melatonin amounts on average to 30 µg with values ranging between 10 and 60 µg in the healthy young adult subjects. These secretions correspond to maximum plasma concentrations, observed from 1 a.m. onwards, ranging between 19 and 94 pg/ml. By extrapolating this correlation between total pineal secretions and maximum plasma melatonin concentrations to the older subjects of the study, the following conclusions can be stated:

The total melatonin secretions by the pineal gland, during the night (duration 8 h, between 10 p.m. and 6 a.m.) vary from 5 µg to 100 µg;

The maximum plasma melatonin concentrations observed from 1 a.m. onwards reflect this secretion; they vary between 10 and 125 pg of melatonin, around a mean value close to 50 pg/ml;

Measurement of the plasma melatonin concentrations, from 1 a.m. onwards, in the patients will make it possible to know the magnitude of their pineal secretion of MLT and, consequently, the state of the [(VLT)-(6-MH)] system in these patients, since MLT is the bioprecursor of the two hormones, valentonin and 6-methoxyharmalan.

3.1 Correlations between melatonin secretions and neurological disorders due to a deficit of the [(VLT)-(6-MH)] system.

Despite the absence in the scientific literature, for technical reasons, of data concerning the magnitude of pineal secretion of melatonin in the various neurological disorders that appear to be connected thereto, it is possible to establish a correlation between pineal MLT secretions and these disorders. Pineal secretion of MLT can be evaluated, as we have just shown, by assaying patients' maximum plasma melatonin concentration from 1 a.m. onwards. The following relationships can be stated:

maximum plasma MLT concentrations below 10 pg/ml, corresponding to pineal MLT secretions below 5 µg, are observed in primary insomnia and in neurodegenerative diseases such as Parkinson's disease. In the particular case of Alzheimer's disease, the very few studies carried out show a collapse of pineal secretion of MLT, with MLT concentrations in biological fluids below the limits of detection of MLT analysis techniques;

maximum plasma MLT concentrations between 10 pg/ml and 50 pg/ml, corresponding to pineal MLT secretions between 5 µg and 25 µg, are observed in sleep disorders and in endogenous and reactive depression.

Thus, the maximum plasma MLT concentration value, reflecting the magnitude of pineal secretion of MLT and, consequently, of pineal secretions of the two hormones of the [(VLT)-(6-MH)] system, can supplement the clinical diagnosis of the neurological disorder and serve as a basis for establishing the dosages of the hormones in the combination (VLT+6-MH) which must be administered transdermally.

The present invention also relates to a method for clinical diagnosis of neurological disorders involving assaying plasma melatonin (MLT) concentrations in a blood sample taken between 10 p.m. and 6 a.m. and preferably from 1 a.m. onwards.

This diagnostic method according to the invention is further characterized in that said assay is carried out by coupling liquid chromatography with mass spectrometry (HPLC-MS/MS). An exemplary implementation of this assay method will be set out below. Exemplary melatonin assay by HPLC-MS/MS.

Chemicals

Melatonin was synthesized by Cerillant and purchased from Promochem (Molsheim, France) and the internal standard, D4-melatonin, was synthesized by CDN Isotopes and purchased from C.I.L. (Sainte-Foix-La-Grande, France). Oasis® HLB SPE cartridges (1 ml, 30 mg) were purchased from Waters (Milford, Mass., USA). HPLC-analyzed methanol, HPLC-analyzed water, analyzed 98-100% formic acid, ultra gradient-grade HPLC-analyzed acetonitrile, HPLC-analyzed methylene chloride, 2 N sodium hydroxide solution and sodium acetate were obtained from Merck AG (Darmstadt, Germany). All the solvents were of high purity and they were used without further purification. In order to avoid any subsequent contamination of the samples, 3.5 ml and 10 ml disposable glass test tubes and 10 ml disposable glass test tubes with Teflon stoppers were used for this analysis.

Calibration Curves

Stock solutions of melatonin and of internal standard were prepared by dissolving each pure reference compound in methanol in order to obtain a primary concentration of 1000 ng/µl. These solutions were stored at −20° C. until use. Working standard solutions, prepared for the analysis, were obtained by suitable dilutions of the stock solutions in methanol and were stored below 20° C. until use.

Various sets of control plasma were tested to establish endogenous melatonin concentrations.

A 9-point calibration curve was prepared each day by loading aliquots (1 ml) of drug-free human plasma with 40 µl of the 5 pg/µl internal standard solution (200 pg of $D_4$-melatonin) and various amounts of melatonin in the range of 1 to 200 pg. Blank samples were prepared in a similar way by loading 1 ml of control plasma alone with the internal standard solution.

Extraction from Plasma Samples

Solid-Phase Extraction

All the SPE experiments were carried out by using a Waters Oasis® HLB column (1 ml, 30 mg). The column was conditioned with 1 ml of methanol, followed by 2 ml of water. Plasma (1 ml), fortified as indicated above with the D4-melatonin solution, was deposited in a 3.5-ml glass test tube and diluted with 1 ml of water. After brief agitation using a vortex mixer, the diluted sample was loaded onto the column. After washing the column with 1 ml of water, the components were eluted with 1 ml of methanol. The samples were evaporated to dryness under a gentle nitrogen stream and dissolved in 1 ml of 0.002 N sodium hydroxide in water.

Liquid-Phase Extraction

After brief agitation using a vortex mixer, 6 ml of methylene chloride was added. The extraction procedure was carried out over a 10-minute period using an alternating agitator. The test tubes were then centrifuged at 4000 rpm for 10 min. The upper aqueous layer was completely removed and the remaining organic phase was transferred to a 10-ml glass test tube and evaporated to dryness at 40° C. under a gentle nitrogen stream. The dry residue was redissolved in 200 µl of water and stored at +4° C. before injection. A fixed volume of 75 µl was injected into the LC-MS/MS system.

Validation Procedure

During this validation procedure, three plasma calibration curves were prepared and preformed the same day by the same analyst. Regression parameters were calculated to evaluate the linearity and reproducibility of the technique. Furthermore, to estimate precision and accuracy during a single day and from one day to the next of the process, repeatability tests were performed at various concentrations (1, 2, 25 and 200 pg/ml) over three separate days. The loaded plasma samples were analyzed over a 1-week period by two different operators and, for each concentration, relative standard deviation and mean percentage error were calculated.

The limit of quantification (LOQ), which must be determined with an indicated confidence level, has been defined as the smallest detectable concentration producing a signal significantly higher than the mean signal measured in representative control samples. First, to calculate the LOQ of the process, a repeatability test was performed with 5 plasma samples, blanks, free of drugs. The mean signal (Ybl) observed at the retention time of melatonin and the associated standard deviation (Sbl) were used to calculate a theoretical value (Yth) of the limit of quantification. Next, a repeatability test was performed with 5 replicates of the plasma samples loaded with a melatonin concentration close to this theoretical limit of quantification. The mean value of the signal (Yloq) was statistically compared with the mean signal (Ybl) obtained with the control samples. After having tested the homogeneity of the variance (p<0.05), Student's t-test or Welch's test was used to show that Yloq was significantly higher than Ybl with 97.5% probability.

To determine the stability of melatonin in frozen human plasma, working solutions were added to a batch of human plasma, blank, and then stored below the freezing temperature of −20° C. Six plasma samples loaded with 2 and 200 pg/ml of melatonin will be extracted and analyzed before and after two and three freeze-thaw cycles. Between each cycle, the samples will be maintained under storage temperature conditions (about −20° C.) identical to those used for normal analysis of the samples.

The plasma extracts will be analyzed repeatedly during the validation period in order to check for possible degradation of the compounds during storage in the solvent at about +4° C. The evaluation of stability is based on the back-calculated concentrations, which should be within ±15% (except for LOQ±20%), and an acceptable chromatographic peak shape.

In order to calculate the total recovery of the process, a plasma calibration curve (from the lower limit of quantification to the upper limit of quantification) will be prepared and analyzed. At the same time, six (6) samples loaded with 2, 25 and 200 pg/ml of melatonin will be extracted and analyzed. The mean values of the response will be calculated and compared with those obtained with the blank plasma extracts (n=6) prepared and loaded with the pure standard at equivalent concentrations at the end of the treatment of the samples. Recovery of the internal standard will also be determined at the concentration used to load the samples.

LC-MS/MS Analysis

Instrument

The HPLC system consisted of an Agilent 1100 series system equipped with a binary pump and a thermostatically-controlled autosampler.

The LC-MS/MS system consisted of a triple quadrupole tandem mass spectrometer (API 4000, Applied Biosystems) operating in Turbo IonSpray positive ionization mode. This system was coupled to the outlet of the HPLC column by means of a length of PEEK tubing.

Chromatographic Conditions

Chromatography was carried out on a C18 column (3.5 µm, 50×2.1 mm ID, XBridge™, Waters, Milford, Mass., USA). The mobile phase was: acetonitrile-5 mM aqueous ammonium acetate-formic acid (25:75:0.01). The flow rate was 0.2 ml/min.

Mass Spectrometer Conditions

The mass spectrometer operated in Turbo IonSpray positive ionization mode at 500° C. The samples were analyzed by selected reaction monitoring (SRM) by employing the transition of the precursor ion [M+H]$^+$ to the product ion for the analyte and the internal standard. The ions monitored in reaction monitoring mode (RMM) were m/z 233.18 (precursor ion: [M+H]$^+$) to 174.10 (product ion) for melatonin and m/z 237.22 (precursor ion: [M+H]$^+$) to 178.10 (product ion) for D4-melatonin (internal standard). The product ions formed are obtained by loss of fragment [NH—CO—CH$_3$].

The ionization voltage was set at +4.8 kV.
The TIS nebulizer gas (gas 1) was set at 40.
The TIS heater gas (gas 2) was set at 50.
The gas curtain was set at 12.
The collision-activated dissociation (CAD) gas was set at 10.
The DP, EP, CE and C×P values were set at 50, 10, 17 and 10, respectively.
The time delay was set at 500 ms for each compound.

Results and Discussion

Pretreatment and Analysis of Samples

The quantitative analysis of a compound present at a very low, femtogram-level concentration in a complex biological fluid represents a colossal challenge for the analyst in charge of a large batch of samples to be analyzed daily. First, the plasma samples must be free of most of the endogenous substances that could interfere with the analysis of melatonin.

We observed that a solid-liquid extraction procedure followed by a liquid-liquid extraction procedure, using a high-purity solvent like methylene chloride in alkaline aqueous phase, led to a clean residue free of most impurities. The extraction process saved a considerable amount of time, so much so that the laboratory was able to process more than 100 additional plasma samples each day. Dissolving the residue in water, which is very protective of the column, made it possible to process a large number of injections daily thanks to a short chromatographic execution time (4.5 min). By using our analytical conditions, the retention time of melatonin and of D4-melatonin was about 2.3 min. Both chromatographic peaks had a Gaussian shape and the peak width at baseline of each analyte was less than 30 s. The peak width at half height was about 5 s. A 500-ms time delay per mass range led to a minimum of 20 data points for the measurement of each compound, taking into account the total inactivity time of the system.

Recovery

The extraction efficiency was about 80% and these results were subsequently confirmed during the HPLC-MS/MS validation procedure.

Total recovery calculated on the basis of the results obtained after replicate analysis of a biological matrix extract and an untreated standard loaded with 200 pg/ml of melatonin:

| Sample no. | Peak area ratio of the biological matrix extract | Untreated standard |
| --- | --- | --- |
| 1 | 1.407 | 1.761 |
| 2 | 1.433 | 1.793 |
| 3 | 1.442 | 1.748 |
| 4 | 1.404 | 1.754 |
| 5 | 1.499 | 1.698 |
| 6 | 1.346 | 1.796 |
| Mean | 1.422 | 1.758 |
| SD | 0.050 | 0.036 |
| n | 6 | 6 |
| RSD (%) | 3.55% | 2.03% |
| Minimum value | 1.346 | 1.698 |
| Maximum value | 1.499 | 1.796 |

Total recovery = 80.85%

Total recovery calculated on the basis of the results obtained after replicate analysis of a biological matrix extract and an untreated standard loaded with 25 pg/ml of melatonin:

| Sample no. | Peak area ratio of the biological matrix extract | Untreated standard |
|---|---|---|
| 1 | 0.169 | 0.221 |
| 2 | 0.173 | 0.208 |
| 3 | 0.173 | 0.213 |
| 4 | 0.187 | 0.210 |
| 5 | 0.179 | 0.211 |
| 6 | 0.169 | 0.211 |
| Mean | 0.175 | 0.212 |
| SD | 0.007 | 0.005 |
| n | 6 | 6 |
| RSD (%) | 3.95% | 2.22% |
| Minimum value | 0.169 | 0.208 |
| Maximum value | 0.187 | 0.221 |

Total recovery = 82.47%

Total recovery calculated on the basis of the results obtained after replicate analysis of a biological matrix extract and an untreated standard loaded with 2 pg/ml of melatonin:

| Sample no. | Peak area ratio of the biological matrix extract | Untreated standard |
|---|---|---|
| 1 | 0.016 | 0.020 |
| 2 | 0.019 | 0.019 |
| 3 | 0.015 | 0.020 |
| 4 | 0.018 | 0.021 |
| 5 | 0.018 | 0.020 |
| 6 | 0.018 | 0.019 |
| Mean | 0.017 | 0.020 |
| SD | 0.002 | 0.001 |
| n | 6 | 6 |
| RSD (%) | 8.90% | 3.82% |
| Minimum value | 0.015 | 0.019 |
| Maximum value | 0.019 | 0.021 |

Total recovery = 87.86%

Linearity of the Calibration Curves

The three plasma calibration curves, obtained the same day by tracing the peak area ratios of melatonin/$D_4$-melatonin as a function of the known melatonin concentrations, were straight lines (mean correlation coefficients±SD=0.9973±0.023) over the concentration range of 1 to 200 pg/ml. The regression analysis intersected close to the origin a mean y-intercept value equal to 0.0035 for n=3 determinations (Table 1). In the third and fifth sets of control plasma samples in the selectivity and specificity test, the mean signal observed in the blank samples was equivalent to 8.38 and 1.47 pg/ml of melatonin. Because of this high level of endogenous melatonin, these control plasma sample sets were not used for the subsequent validation procedure. The RSD value (1.96%) calculated on the basis of the average slope and the associated standard deviation (0.0068±0.0001) show the reproducibility of the technique over the course of the same day. Linearity and reproducibility from day to day were evaluated by using the regression parameters of 5 calibration curves prepared and performed over a 1-week period by two different analysts. These calibration curves were prepared with the same set of control plasmas. As shown in Table 2, the mean value of the slope (0.0069±0.0001) was close to the "linearity test" over one day and there was very little dispersion of the 5 calibration points along the regression plots (Table 2).

TABLE 1

Parameters of the calibration curve over the course of the same day obtained during the "linearity test" over one day

| Curve | Slope | y-Intercept | Determination factor |
|---|---|---|---|
| 1 | 0.0069 | 3.3500E−03 | 0.9995 |
| 2 | 0.0067 | 3.1700E−03 | 0.9992 |
| 3 | 0.0069 | 4.0800E−03 | 0.9997 |
| Mean | 0.0068 | 0.0035 | 0.9995 |
| SD | 0.0001 | 0.0006 | 0.0004 |
| n | 2 | 2 | 2 |
| RSD (%) | 1.96% | * | 0.04% |
| Minimum value | 0.0067 | 3.1700E−03 | 0.9992 |
| Maximum value | 0.0069 | 4.0800E−03 | 0.9997 |

TABLE 2

Linearity and reproducibility from day to day of 5 plasma calibration curves prepared and performed over a 1-week period

| Curve | Slope | y-Intercept | Determination factor |
|---|---|---|---|
| Series 2 | 0.0070 | 3.7900E−03 | 0.9973 |
| Series 3 | 0.0068 | 4.8000E−03 | 0.9972 |
| Series 4-1 | 0.0069 | 3.3500E−03 | 0.9995 |
| Series 4-2 | 0.0067 | 3.1700E−03 | 0.9992 |
| Series 4-3 | 0.0069 | 4.1000E−03 | 0.9997 |
| Mean | 0.0069 | 0.0038 | 0.9986 |
| SD | 0.0001 | 0.0006 | 0.0012 |
| n | 5 | 5 | 5 |
| RSD (%) | 1.66% | * | 0.12% |
| Minimum value | 0.0067 | 0.0032 | 0.9972 |
| Maximum value | 0.0070 | 0.0048 | 0.9995 |

Precision and Accuracy

All the sources of variability were substantially reduced thanks to the use of a pure stable isotope analog as internal standard. The relative standard deviations of the various plasma repeatability tests calculated over three separate days were below 15.2% and the mean percentage errors were in the range of −9.71% to +4.61% (Tables 3).

TABLE 3.1

Precision and accuracy over the course of the same day of the HPLC-MS/MS process calculated over three separate days

| Theoretical concentration (pg/ml) | n | Experimental concentration (pg/ml) | Mean (pg/ml) | SD | RSD (%) | Bias (%) |
|---|---|---|---|---|---|---|
| 1 | 6 | 0.875 | 1.016 | 0.145 | 14.23 | 1.58 |
|  |  | 1.096 |  |  |  |  |
|  |  | 0.834 |  |  |  |  |
|  |  | 0.968 |  |  |  |  |
|  |  | 1.179 |  |  |  |  |
|  |  | 1.143 |  |  |  |  |
| 2 | 6 | 1.993 | 1.806 | 0.150 | 8.33 | −9.71 |
|  |  | 1.830 |  |  |  |  |
|  |  | 1.634 |  |  |  |  |
|  |  | 1.949 |  |  |  |  |
|  |  | 1.789 |  |  |  |  |
|  |  | 1.641 |  |  |  |  |

TABLE 3.1-continued

Precision and accuracy over the course of the same day of the HPLC-MS/MS process calculated over three separate days

| Theoretical concentration (pg/ml) | n | Experimental concentration (pg/ml) | Mean (pg/ml) | SD | RSD (%) | Bias (%) |
|---|---|---|---|---|---|---|
| 25 | 6 | 24.586 | 24.101 | 0.450 | 1.87 | -3.60 |
|  |  | 24.378 |  |  |  |  |
|  |  | 23.413 |  |  |  |  |
|  |  | 24.168 |  |  |  |  |
|  |  | 24.356 |  |  |  |  |
|  |  | 23.706 |  |  |  |  |
| 200 | 6 | 213.318 | 209.213 | 3.681 | 1.76 | 4.61 |
|  |  | 209.294 |  |  |  |  |
|  |  | 213.664 |  |  |  |  |
|  |  | 205.029 |  |  |  |  |
|  |  | 208.338 |  |  |  |  |
|  |  | 205.633 |  |  |  |  |

TABLE 3.2

Precision and accuracy over the course of the same day of the HPLC-MS/MS process calculated over three separate days

| Theoretical concentration (pg/ml) | n | Experimental concentration (pg/ml) | Mean (pg/ml) | SD | RSD (%) | Bias (%) |
|---|---|---|---|---|---|---|
| 1 | 6 | 1.101 | 1.035 | 0.146 | 14.07 | 3.50 |
|  |  | 1.292 |  |  |  |  |
|  |  | 0.932 |  |  |  |  |
|  |  | 0.960 |  |  |  |  |
|  |  | 0.897 |  |  |  |  |
|  |  | 1.028 |  |  |  |  |
| 2 | 6 | 1.751 | 1.926 | 0.219 | 11.39 | -3.71 |
|  |  | 2.225 |  |  |  |  |
|  |  | 1.602 |  |  |  |  |
|  |  | 1.973 |  |  |  |  |
|  |  | 2.029 |  |  |  |  |
|  |  | 1.974 |  |  |  |  |
| 25 | 6 | 23.465 | 24.339 | 0.983 | 4.04 | -2.64 |
|  |  | 24.003 |  |  |  |  |
|  |  | 24.109 |  |  |  |  |
|  |  | 26.021 |  |  |  |  |
|  |  | 24.938 |  |  |  |  |
|  |  | 23.496 |  |  |  |  |
| 200 | 6 | 199.391 | 201.479 | 7.163 | 3.56 | 0.74 |
|  |  | 203.061 |  |  |  |  |
|  |  | 204.356 |  |  |  |  |
|  |  | 198.973 |  |  |  |  |
|  |  | 212.388 |  |  |  |  |
|  |  | 190.702 |  |  |  |  |

TABLE 3.3

Precision and accuracy over the course of the same day of the HPLC-MS/MS process calculated over three separate days

| Theoretical concentration (pg/ml) | n | Experimental concentration (pg/ml) | Mean (pg/ml) | SD | RSD (%) | Bias (%) |
|---|---|---|---|---|---|---|
| 1 | 6 | 1.040 | 0.998 | 0.151 | 15.15 | -0.18 |
|  |  | 0.887 |  |  |  |  |
|  |  | 1.171 |  |  |  |  |
|  |  | 1.159 |  |  |  |  |
|  |  | 0.796 |  |  |  |  |
|  |  | 0.938 |  |  |  |  |
| 2 | 5 | 1.825 | 1.906 | 0.200 | 10.50 | -4.72 |
|  |  | 1.730 |  |  |  |  |
|  |  | 1.810 |  |  |  |  |
|  |  | *2.883 |  |  |  |  |
|  |  | 1.921 |  |  |  |  |
|  |  | 2.242 |  |  |  |  |
| 25 | 6 | 23.994 | 24.424 | 0.465 | 1.90 | -2.30 |
|  |  | 24.003 |  |  |  |  |
|  |  | 24.221 |  |  |  |  |
|  |  | 25.139 |  |  |  |  |
|  |  | 24.361 |  |  |  |  |
|  |  | 24.827 |  |  |  |  |
| 200 | 6 | 201.641 | 206.482 | 2.559 | 1.24 | 3.24 |
|  |  | 208.259 |  |  |  |  |
|  |  | 206.438 |  |  |  |  |
|  |  | 207.900 |  |  |  |  |
|  |  | 206.162 |  |  |  |  |
|  |  | 208.489 |  |  |  |  |

The results of the repeatability analyses from day to day were quite similar to those obtained during the analysis over the course of the same day: the RSD values were below 13.68% and the mean percentage error was in the range of −6.13 to +2.86% for the melatonin concentrations tested (from 1 to 200 pg/ml) (Table 4).

TABLE 4

Precision and accuracy from day to day of the HPLC-MS/MS process calculated over a 1-week period during the repeatability analyses

| Theoretical concentration (pg/ml) | n | Mean (pg/ml) | SD | RSD (%) | Bias (%) | Mean RSD (%) |
|---|---|---|---|---|---|---|
| 1 | 18 | 1.016 | 0.139 | 13.68 | 1.64 | 14.48 |
| 2 | 17 | 1.877 | 0.188 | 9.99 | -6.13 | 10.08 |
| 25 | 18 | 24.288 | 0.653 | 2.69 | -2.85 | 2.60 |
| 200 | 18 | 205.724 | 5.645 | 2.74 | 2.86 | 2.18 |

Limits of Quantification

A signal-to-noise ratio >3 is a value still used by many authors as a criterion for a significant response. Unfortunately, even if electronic noise is relatively constant from day to day, that is not always true for chemical background noise, which is sometimes drastically different from one determination to the next. This is mainly due to the sample itself, to the solvents, to the extraction material and to the chromatographic system. In order to take into account all these sources of variability, we used a statistical determination of the limit of quantification. The theoretical LOQ, based on the results obtained after the HPLC-MS/MS analysis of five different control samples, was calculated as being equal to Yth=0.25 pg/ml.

Because of the presence of endogenous melatonin in the blank samples, a repeatability analysis was performed at a higher concentration equal to 1 pg/ml. Student's t-test was applied to show that the mean value of the signal YLOQ±SD (1.069E-02±7.405E-04) calculated on the basis of the repeatability analysis performed at 1 pg/ml was significantly different from that (Ybl) observed with the 5 blank samples (2.663E-03±2.760E-04). $t_{cal}$=22.5, standard deviation=0.563E-03 for n=8 degrees of freedom. The probability of the result, under the null hypothesis, is equal to 0.00. Because of the very small RSD (1.16%) and mean percentage error (−0.40%), this concentration was of course validated as the limit of quantification of the process (Table 5).

A standard mass chromatogram was recorded after HPLC-MS/MS analysis of a control plasma sample. Endogenous melatonin was present in this sample at a concentration below 0.25 pg/ml. The mass chromatograms of the control samples loaded with 1 (LOQ) and 200 pg/ml of melatonin were obtained. When a plasma extract corresponding to the LOQ of the process was analyzed, the signal measured at the retention time of melatonin was equivalent to about 375 fg injected into the HPLC-MS/MS system. Endogenous melatonin, measured in the control samples, generates a signal. It becomes obvious that melatonin concentrations below 0.25 pg/ml can be quantified, during clinical testing, with high precision and accuracy as shown by the results of the repeatability analysis (RSD=10.36%) performed with the 5 blank samples.

TABLE 5

Validation procedure for determining LOQ at the pg/ml level

| Sample no. | Peak area ratio of the blank sample extract | Peak area ratio of the LOQ sample extract | Back-calculated concentration in pg/ml of the LOQ sample extract |
| --- | --- | --- | --- |
| 1 | 2.29E−03 | 1.08E−02 | 0.990 |
| 2 | 3.06E−03 | 1.08E−02 | 1.009 |
| 3 | 2.59E−03 | 1.02E−02 | 1.000 |
| 4 | 2.68E−03 | 9.76E−03 | 0.979 |
| 5 | 2.70E−03 | 1.10E−02 | 1.002 |
| Mean | $Y_{b1}$ = 2.663E−03 | $Y_{loq}$ = 1.069E−02 | 0.996 |
| SD | 2.760E−04 | 7.405E−04 | 0.012 |
| n | 5 | 5 | 5 |
| RSD (%) | 10.36% | 6.93% | 1.16% |
| Minimum value | 2.29E−03 | 9.76E−03 | 0.979 |
| Maximum value | 3.06E−03 | 1.17E−02 | 1.009 |

Reproducibility of the Injection

The reproducibility of the injection step was also studied at one concentration (200 pg/ml) and the results of this test are summarized in Table 6. When the same plasma extract was injected repeatedly (n=100), the RSD values were below 1.0%, thus showing that the process was suitable for an exact analysis of melatonin. Furthermore, no memory effect was observed in the blank sample analyzed after injection of the plasma extract containing 200 pg/ml of melatonin.

TABLE 6

Reproducibility of the injection

| Sample no. | Retention time of melatonin | Peak area of melatonin | Retention time of the internal standard | Peak area of the internal standard | Peak area ratio |
| --- | --- | --- | --- | --- | --- |
| Mean | 2.33 | 232940 | 2.29 | 370240 | 0.63 |
| SD | 0.01 | 5344 | 0.01 | 10734 | 0.01 |
| RSD (%) | 0.49% | 2.29% | 0.49% | 2.90% | 0.99% |
| n | 100 | 100 | 100 | 100 | 100 |
| Minimum value | 2.31 | 221000 | 2.28 | 348000 | 0.62 |
| Maximum value | 2.36 | 241000 | 2.33 | 385000 | 0.64 |

Stability Test

Stability During Freeze-Thaw Cycles

The results of this stability test (Tables 7 and 8) clearly showed that freeze-thaw cycles have no effect on the stability of melatonin in human plasma samples stored at about −20° C.

TABLE 7

| Reference concentration (pg/ml) | n | Experimental concentration (pg/ml) | Mean (pg/ml) | SD | RSD (%) | Bias as a function of the theoretical concentration (%) |
| --- | --- | --- | --- | --- | --- | --- |
| 1.806 | 6 | 1.862 | 1.898 | 0.087 | 4.59 | 5.10 |
|  |  | 1.957 |  |  |  |  |
|  |  | 2.044 |  |  |  |  |
|  |  | 1.812 |  |  |  |  |
|  |  | 1.833 |  |  |  |  |
|  |  | 1.880 |  |  |  |  |
| 209.213 | 6 | 208.926 | 211.083 | 4.957 | 2.35 | 0.89 |
|  |  | 211.252 |  |  |  |  |
|  |  | 209.417 |  |  |  |  |
|  |  | 219.452 |  |  |  |  |
|  |  | 212.865 |  |  |  |  |
|  |  | 204.588 |  |  |  |  |

TABLE 8

Analysis of the stability of melatonin after freeze-thaw cycles: precision and bias of measurements of biological matrix of melatonin after 3 freeze-thaw cycles

| Reference concentration (pg/ml) | n | Experimental concentration (pg/ml) | Mean (pg/ml) | SD | RSD (%) | Bias as a function of the theoretical concentration (%) |
| --- | --- | --- | --- | --- | --- | --- |
| 1.806 | 5 | 1.889 | 1.895 | 0.147 | 7.78 | 4.96 |
|  |  | 1.743 |  |  |  |  |
|  |  | 1.776 |  |  |  |  |
|  |  | *48.99 |  |  |  |  |
|  |  | 2.108 |  |  |  |  |
|  |  | 1.960 |  |  |  |  |
| 209.213 | 6 | 207.575 | 208.003 | 3.079 | 1.48 | −0.58 |
|  |  | 211.163 |  |  |  |  |
|  |  | 203.999 |  |  |  |  |
|  |  | 205.980 |  |  |  |  |
|  |  | 207.232 |  |  |  |  |
|  |  | 212.067 |  |  |  |  |

Stability of the Plasma Extract

The results presented in Table 9 show that the sample extracts were stable in the injection solvent when the injection vials were stored at about +4° C. for at least 24 hours after the first injection for melatonin. No decrease in signal intensity or modification of the chromatographic traces was observed.

TABLE 9

Post-preparatory stability. CQs loaded with melatonin at two concentrations (2 and 200 pg/ml) were stored on an autosampler and reanalyzed (working conditions for the analysis)

| Day | 2 pg/ml | 200 pg/ml |
|---|---|---|
| T0 (series 2) | 1.751 | 199.391 |
|  | 2.225 | 203.061 |
|  | 1.602 | 204.356 |
|  | 1.973 | 198.973 |
|  | 2.029 | 212.388 |
|  | 1.974 | 190.702 |
| Mean | 1.926 | 201.479 |
| T0 + 24 h (series 3) | 1.817 | 201.388 |
|  | 1.908 | 213.337 |
|  | 1.800 | 205.171 |
|  | 2.560 | 207.755 |
|  | 1.806 | 208.103 |
|  | 1.854 | 213.387 |
| Mean | 1.958 | 208.190 |
| Deviation T0 + 24 h/T0 | 1.65% | 3.33% |

3.2 Calculation of the ratio between the doses of VLT and 6-MH administered in the combination, for 8 hours, starting at 10 p.m. (or at bedtime), for ensuring the prevalence of VLT concentrations in the body during the rest period (between 10 p.m. and 6 a.m.), and then the prevalence of 6-MH concentrations from 6 a.m. (or upon rising), through the activity period, until 10 p.m.

In order to guarantee the prevalence of VLT concentrations in the body, during the rest period between 10 p.m. (or at bedtime) and 6 a.m. (or upon rising), and then that of 6-MH throughout the activity period, between rising and bedtime, it is necessary to inject into the body, during the application period of the patch, doses of VLT and 6-MH whose values must have a Bioavailable dose of VLT/Bioavailable dose of 6-MH ratio that ensures the prevalences and the alternation thereof throughout the nychthemeron. This ratio of bioavailable doses can be calculated from their pharmacokinetic parameters, as indicated below.

By setting a bioavailable dose equal to 40 µg of VLT, a median dose which appears to us suited to the treatment of primary insomnia and neurodegenerative disorders like Parkinson's disease, corresponding to low pineal secretion of MLT (secretion below 5 µg of MLT and plasma MLT concentration from 1 a.m. onwards below 10 pg/ml), it is possible to calculate the bioavailable dose of 6-MH to be coadministered in order to ensure the prevalences of the two hormones and the alternation thereof during the rest and activity periods.

During constant-rate (zero-order pharmacokinetics) infusion of VLT (or 6-MH) into the bloodstream, plasma VLT concentrations gradually increase until they reach a plateau where the elimination rate becomes equal to the infusion rate. Consequently, incoming VLT equals outgoing VLT and plasma concentrations are held constant. This is the "plateau" state. If the amount of VLT infused over an 8-hour period is equal to 40 µg, we can write, at the plateau state:

Infusion rate (of VLT)=40 µg/8 h=Elimination rate (of VLT)=CL×$C_{ss}$,   Relationship 1:

a relationship in which CL is total clearance (or plasma clearance, expressed in liters per hour (1/h));

with CL=$(0.693/T_{1/2}z) \times V_d ss$, a relationship in which $V_d$ss is the volume of distribution at steady state (ss), which corresponds to the plateau state, above which plasma VLT concentrations increase no further (from 1 a.m. onwards) and remain at a plateau (the steady state) at their maximum $C_{ss}$ value.

The pharmacokinetic study of VLT and 6-MH carried out in dogs, after intravenous administration of a combination of VLT (3 mg/kg) and 6-MH (1 mg/kg) made it possible to determine the pharmacokinetic parameter values shown below:

VLT:
$T_{1/2}z$=0.70 h
$V_d$ss=5 liters/kg of body weight, or 320 liters for a body weight of 64 kg in humans.

6-MH:
$T_{1/2}z$=2.27 h
$V_d$ss=15 liters/kg of body weight, or 960 liters for a body weight of 64 kg in humans.

As the pharmacokinetic profiles, i.e., the pharmacokinetic parameter values, are identical in humans and dogs, just as in all diurnal animals, it is possible to extrapolate to humans the PK parameter values observed in dogs.

The prevalence and alternation of concentrations of the two hormones during the rest and activity periods must be assured not only in the blood (plasma concentrations), but also at their sites of action (5-$HT_{2c}$, $\alpha_2$, $D_1$ and $D_2$ receptor sites, etc.). It is thus necessary to take into account the volume of distribution ($V_d$ss) values of the two hormones, which link the plasma concentrations of the hormones to their concentrations at their sites of action.

Calculation of the maximum plasma concentration ($C_{ss}$) of VLT for an infused amount of VLT equal to 40 µg in humans. According to the above-mentioned relationship 1, one may write:

$$C_{ss}(VLT) = \frac{40 \ \mu g \times 0.70 \ h}{0.693 \times 8 \ h \times 320 \ l} = 15.8 \ pg/ml, \text{ for } VLT.$$

For 6-MH, which has a volume of distribution three times higher than that of VLT, maximum plasma concentrations ($C_{ss}$) must be maintained at values one-third those of VLT in order to maintain the prevalence of 6-MH concentrations, during the rest period, both in the plasma and peripherally at receptor sites. To that end, the infused dose of 6-MH, combined with an infused dose of 40 µg of VLT, should not exceed 10 µg. Indeed, for an infused dose of 10 µg, we have:

$$C_{ss}(6\text{-}MH) = \frac{10 \ \mu g \times 2.27 \ h}{0.693 \times 8 \ h \times 960 \ l} = 4.3 \ pg/ml, \text{ for } 6\text{-}MH.$$

Taking into account a volume of distribution three times higher than that of VLT, the maximum 6-MH concentrations near the receptors will always be below those of VLT during the rest period.

In conclusion, to guarantee the prevalences of the two hormones (VLT and 6-MH) and the alternation thereof, it is necessary to infuse into the bloodstream VLT doses at least four times higher than those of 6-MH.

According to another particular aspect of the present invention, the adhesive transdermal therapeutic system contains a combination of a load of valentonin (VLT) and of 6-methoxyharmalan (6-MH) capable of delivering into the bloodstream a combination of valentonin and 6-methoxyharmalan in a [VLT]/[6-MH] mass proportion at least equal to 4 during the application period of the patch, preferably for about 8 to 10 hours.

As for the level, i.e., the order of magnitude, of the doses, we used as a base the pineal melatonin secretion values measured in humans.

For the treatment of sleep disorders and endogenous and reactive depression, disorders characterized by maximum plasma MLT concentrations, measured in patients from 1 a.m. onwards, between 10 pg/ml and 50 pg/ml, it is recommended to apply a patch at bedtime (around 10 p.m. or later according to habits), with a load of VLT and of 6-MH that delivers to the body doses equal to 20 µg of VLT and 5 µg of 6-MH, during the application period of the patch, between 8 and 10 hours, depending on the hour of rising, at which time the patch must be removed.

According to another particular aspect of the invention, the adhesive transdermal therapeutic system contains a load of VLT and of 6-MH that delivers into the bloodstream a dose of at least 20 µg of VLT and at least 5 µg of 6-MH throughout the application period of the patch, preferably for about 8 to 10 hours, for use in the treatment of sleep disorders and depression.

For the treatment of primary insomnia and neurodegenerative diseases such as Parkinson's disease, diseases characterized by maximum plasma MLT concentrations, measured in patients from 1 a.m. onwards, below 10 pg/ml, it is recommended to apply a patch at bedtime (around 10 p.m., or later according to habits), with a load of VLT and of 6-MH that delivers to the body doses equal to 40 µg of VLT and 10 µg of 6-MH during the application period of the patch, between 8 and 10 hours, depending on the hour of rising, at which time the patch must be removed.

According to another feature of the invention, the adhesive transdermal therapeutic system contains a load of VLT and of 6-MH that delivers into the bloodstream a dose of at least 40 µg of VLT and at least 10 µg of 6-MH during the application period of the patch, preferably for about 8 to 10 hours, for the treatment of primary insomnia and/or Parkinson's disease-type conditions.

For the treatment of Alzheimer's-type neurodegenerative diseases, diseases characterized by maximum plasma MLT concentrations, measured in patients from 1 a.m. onwards, below 1 pg/ml, or even unmeasurable, it is recommended to apply a patch at bedtime (around 10 p.m., or later according to habits), with a load of VLT and of 6-MH, during the application period of the patch, between 8 and 10 hours depending on the hour of rising, at which time the patch must be removed.

According to another particular aspect of the invention, the adhesive transdermal therapeutic system contains a load of VLT and of 6-MH that delivers into the bloodstream a dose of at least 60 µg of VLT and at least 15 µg of 6-MH during the application period of the patch, preferably for about 8 to 10 hours, for use in the prevention and/or treatment of Alzheimer's disease.

As already indicated, the present invention also extends to the treatment of conditions due to excessive pineal secretion of the hormones of the [(VLT)-(6-MH)] system. The particular case of the treatment of psychosis consists in applying, during the activity period, a patch loaded only with valentonin. VLT should displace the excess 6-methoxyharmalan secreted in psychotic patients.

The invention claimed is:

1. An adhesive transdermal therapeutic system, containing as active ingredient a combination of valentonin (VLT) and 6-methoxyharmalan (6-MH), wherein the application period of the patch is from 8 to 10 hours, and wherein the system delivers the VLT and the 6-MH at a constant-rate infusion rate for a period of 8 to 10 hours.

2. The adhesive transdermal therapeutic system according to claim 1, containing a combination of a load of valentonin (VLT) and of 6-methoxyharmalan (6-MH) capable of delivering into the bloodstream valentonin and 6-methoxyharmalan in a [VLT]/[6-MH] mass proportion at least equal to 4 during the application period of the patch.

3. The adhesive transdermal therapeutic system according to claim 1, wherein the active ingredient consists of the VLT and the 6-MH.

4. A method for the treatment of sleep disorders and depression, comprising the application to a person in need thereof of the adhesive transdermal therapeutic system according to claim 1, containing a load of VLT and of 6-MH that delivers into the bloodstream a dose of at least 20 µg of VLT and at least 5 µg of 6-MH during the application period of the patch.

5. The method according to claim 4, wherein the application period of the patch is from 8 to 10 hours.

6. A method for the treatment of primary insomnia and/or Parkinson's disease-type conditions, comprising the application to a person in need thereof of the adhesive transdermal therapeutic system according to claim 1, containing a load of VLT and of 6-MH that delivers into the bloodstream a dose of at least 40 µg of VLT and at least 10 µg of 6-MH during the application period of the patch.

7. The method according to claim 6, wherein the application period of the patch is from 8 to 10 hours.

8. A method for the treatment of Alzheimer's disease, comprising the application to a person in need thereof of the adhesive transdermal therapeutic system according to claim 1, containing a load of VLT and of 6-MH that delivers into the bloodstream a dose of at least 60 µg of VLT and at least 15 µg of 6-MH during the application period of the patch.

9. The method according to claim 8, wherein the application period of the patch is from 8 to 10 hours.

10. A method for the treatment of sleep disorder and/or depression symptom associated with Alzheimer's disease, comprising the application to a person in need thereof of the adhesive transdermal therapeutic system according to claim 1, containing a load of VLT and of 6-MH that delivers into the bloodstream a dose of at least 60 µg of VLT and at least 15 µg of 6-MH during the application period of the patch.

11. A method for the treatment of Alzheimer's disease comprising the application to a person in need thereof the adhesive transdermal therapeutic system according to claim 1, containing as active ingredient a combination of valentonin (VLT) and 6-methoxyharmalan (6-MH) during a period of from 8 to 10 hours.

* * * * *